United States Patent [19]

Alam

[11] Patent Number: 5,635,045

[45] Date of Patent: Jun. 3, 1997

[54] APPARATUS FOR, AND A METHOD OF, ELECTROELUTION ISOLATION OF BIOMOLECULES AND RECOVERING BIOMOLECULES AFTER ELUTION

[76] Inventor: Aftab Alam, 9 Foxcliffe Court, St. Louis, Mo. 63011

[21] Appl. No.: 221,109

[22] Filed: Mar. 31, 1994

Related U.S. Application Data

[63] Continuation-in-part of Ser. No. 63,731, May 20, 1993, abandoned.

[51] Int. Cl.$^6$ .................................................. C25B 7/00
[52] U.S. Cl. ..................... 204/462; 204/456; 204/466; 204/606; 204/613; 204/614; 204/616
[58] Field of Search ........................... 204/180.1, 182.8, 204/299 R, 182.3, 301, 456, 462, 466, 606, 613, 614, 616

[56] References Cited

U.S. PATENT DOCUMENTS

| | | | |
|---|---|---|---|
| 4,552,640 | 11/1985 | Kartenbeck | 204/301 |
| 4,617,102 | 10/1986 | Tomblin et al. | 204/299 R |
| 4,699,706 | 10/1987 | Burd et al. | 204/301 |
| 4,707,233 | 11/1987 | Margolis | 204/182.3 |
| 4,863,582 | 9/1989 | Wijangco et al. | 204/299 R |
| 4,964,961 | 10/1990 | Brautigam et al. | 204/182.3 |
| 5,102,518 | 4/1992 | Doering et al. | 204/180.1 |
| 5,340,449 | 8/1994 | Shukla | 204/180.1 |
| 5,384,022 | 1/1995 | Rajasekaran | 204/299 R |
| 5,538,614 | 7/1996 | Han | 204/613 |

OTHER PUBLICATIONS

Matthew J. Pollman and Anthony J. Zuccarelli, Analytical Biochemistry, *Rapid Isolation of High–Molecular–Weight DNA from Agarose Gels* 180, 12–17 (1989).

Henrich Hansen and Hilmar Lemke, BioTechniques, *Rapid and Simple Purification of PCR Products by Direct Band Elution During Agarose Gel Electrophoresis* vol. 14, pp. 28–29 (1993).

Duro et al., Analytical Biochemistry, *A method for Eluting DNA in a Wide Range of Molecular Weights from Agarose Gels* vol. 195, pp. 111–115 (1991).

Lida Zhen and Richard T. Swank, BioTechniques, *A Simple and High Yield Method for Recovering DNA from Agarose Gels* vol. 14, pp. 894–898 (1993).

Yang et al., Methods in Enzymology *Elution of DNA from Agarose Gels after Electrophoresis* vol. 68, pp. 176–182 (1979).

Gel Electrophoresis, *Little Blue Tank*, Isco, Inc. USA, Catalog 28, pp. 37–39 (1993).

Electro–Eluter/Concentrator, C.B.S. Scientific Company, pp. 36–37 (1993).

Biometra, *UV Band–Elutor . . . A Really New Technique in Nucleic Acid Electrophoresis*, D–3400 Göttingeu, Germany, (1993).

Biometra, *HSB Elutor (patented) Membrane Free Elution of Nucleic Acids From Gels*, D–3400 Göttingeu, Germany, (1993).

Bio Rad Lab *Model 422 Electro–Eluter*, p. 276 (1993).

Analytical Biochemistry, *An Ultrarapid Method for the Recovery of DNA from Gels*, pp. 209–212 (1993).

Hoefer Scientific Instruments, *SixPAC™ Electroelution Unit GE 200*, p. 48 (1994).

Abstract from USSR; from Otkrytiya, Izobret. 1986, (38), 278.

*Primary Examiner*—Howard L. Schain
*Assistant Examiner*—C. Delacroix-Muirheid
*Attorney, Agent, or Firm*—Watson, Cole, Stevens, Davis, P.L.L.C.

[57] ABSTRACT

An apparatus for electroelution isolation of biomolecules and recovering biomolecules after elution including a tubular enclosure for engaging a piece of separating gel having a band of biomolecules. The enclosure is capped by a closure means having a passage means, and then placed in an electrophoresis tank with the closure means facing the positive terminal. Applying an electric current forces the biomolecules to accumulate at the closure means. The biomolecules may be recovered by inserting a capillary tip through the passage means and drawing the biomolecules through the capillary.

43 Claims, 4 Drawing Sheets

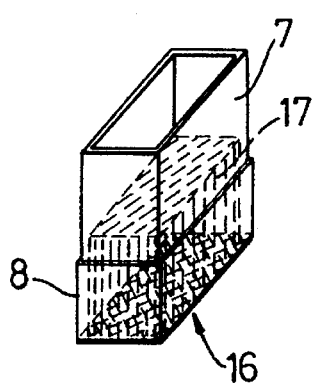
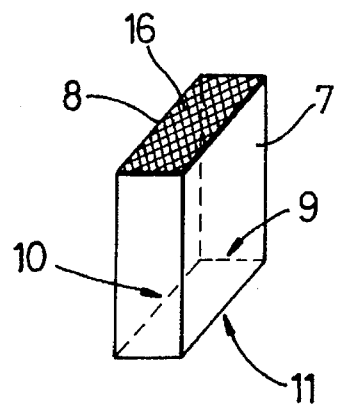
Fig. 7    Fig. 8
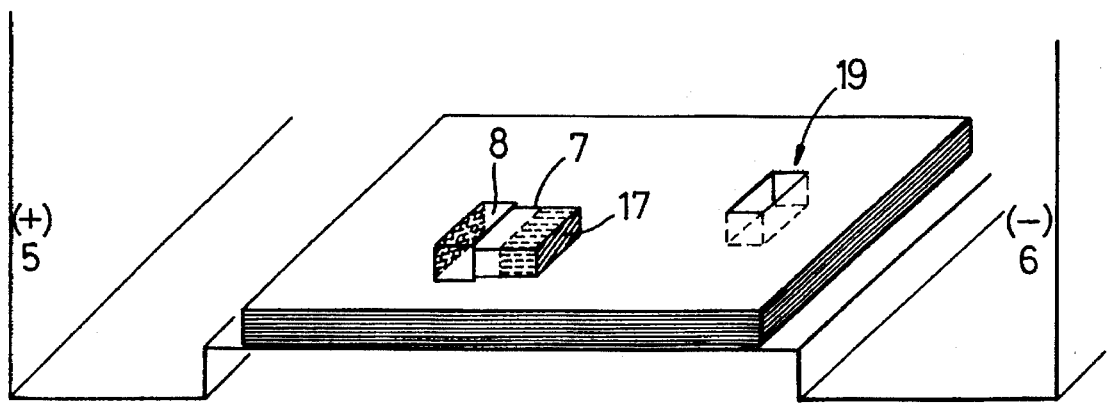
Fig. 9

APPARATUS FOR, AND A METHOD OF, ELECTROELUTION ISOLATION OF BIOMOLECULES AND RECOVERING BIOMOLECULES AFTER ELUTION

CROSS-REFERENCE TO RELATED APPLICATION

This application is a continuation-in-part of Applicant's application Ser. No. 08/063,731, filed May 20, 1993, now abandoned.

FIELD OF THE INVENTION

This invention relates to an apparatus for, and a method of, electroelution isolation of biomolecules and recovering biomolecules after elution, and more specifically to using a submerged horizontal electrophoresis device for both analytical electrophoresis and electroelution isolation of biomolecules.

BACKGROUND AND SUMMARY OF THE INVENTION

During electrophoresis of biomolecules such as protein and nucleic acids (DNA & RNA), the biomolecules separate into distinct bands. One of the methods for isolation of a single species of protein, nucleic acids, and the like is electrophoresis followed by electroelution of a single electrophoresis band. There are various devices currently available for electroelution but they all include one common step: the band for electroelution must first be cut away from the separating gel and then loaded for electroelution in an electroelution device. Electroelution devices are engineered distinctly separate from the devices used for analytical electrophoresis and the use of such an electroelution device requires additional preparation and additional steps such as, setting up the device, preparation of reagents, loading of samples, setting up the running condition, and a procedure for recovery of electroeluted samples. Electroelution has historically been a laborious method, and the devices used have been difficult to operate.

Analytical electrophoresis of nucleic acids is most commonly performed by submerged horizontal electrophoresis. As the name implies, a gel is submerged horizontally in an electrophoresis tank. Samples are applied in preformed wells in the gel, and when electrical current is applied across the gel, nucleic acid molecules migrate toward the positive terminal and separate into distinct size-dependent bands. In the prior art, recovery of the nucleic acid from any of the bands required excision of the band followed by either chemical extraction or electroelution in a separate electroelution device.

As disclosed in the parent, following electrophoretic separation of biomolecules such as protein, nucleic acids and the like into distinct bands, electroelution is performed by engaging a piece of the separating gel containing the band of biomolecules intended for electroelution in a tubular enclosure. Preferably, the tubular enclosure has a rectangular cross section and the enclosure interior is substantially the same shape and size as the piece of separating gel containing the band of biomolecules intended for electroelution. Having a tubular enclosure with an interior shape and size substantially the same as the piece of separating gel containing the band of biomolecules intended for electroelution forms a piece of separating gel which fits into the tubular enclosure like a plug. The gel piece forms a substantially liquid impervious seal with the enclosure and partitions the buffer in the tubular enclosure from the buffer between the piece of gel and the closure means. After electroelution, the buffer in the tubular enclosure can be removed without disturbing the electroeluted biomolecules in the closure means. Such a tubular enclosure eliminates the need for a septum in the tubular enclosure for separating the gel pieces in the tubular enclosure from the buffer in the closure means. The piece of separating gel itself acts as a septum. Furthermore, the tubular enclosure is minimized to the size and volume equal to the piece of separating gel. It is also possible to have a tubular enclosure in which a blank piece of gel (i.e., a gel piece without any molecules for electroelution) is engaged. In this case, the blank piece of gel acts as a plug, and the pieces of gel having molecules for electroelution are loaded behind the blank piece of gel.

The tubular enclosure is provided with a closure means for preventing the passage of biomolecules (such as nucleic acid and the like) out of the tubular enclosure without hindering the electrophoresis electrical field. The closure means may be either an integral part of the tubular enclosure or demountable from the tubular enclosure. Preferably, the closure means is demountable from the tubular enclosure, and the closure means is positioned on the tubular enclosure after engaging a piece of separating gel into the tubular enclosure.

As disclosed in the parent, the closure means has an open end and an opposite end over which a semipermeable membrane, such as a dialysis membrane is secured. Other types of closure means membranes may also be used, such as an ion exchange membrane or other types of binding membranes, as long as the closure means membrane prevents the passage of nucleic acids and the like out of the tubular enclosure without hindering the electrical field of electrophoresis. The closure means membrane may be secured to the tubular enclosure or demountable closure means by using glue, a sleeve member, or other suitable means.

The inventor has improved upon the invention disclosed in the parent by providing a closure means having a passage means for reaching behind the closure means membrane and recovering the biomolecules accumulated against the closure means membrane during electroelution. "Behind the closure means membrane" and "behind the membrane" hereinafter refer to the face of the membrane where electroeluted biomolecules accumulate. The passage means is preferably an opening adjacent to the closure means opposite end. The passage means may be closed by the closure means membrane but is preferably closed by a separate membrane. If the closure means membrane is used to cover the passage means, a sleeve member is preferably used to secure the membrane over both the closure means and the passage means.

After electroelution is complete, the passage means may be opened by rupturing the membrane which covers the passage means. A pipette tip may be introduced through the passage means in order to reach behind the closure means membrane. The pipette tip is preferably positioned along side the closure means membrane and a thin film of buffer containing the electroeluted biomolecules is removed. The pipette tip used for reaching behind the closure means membrane preferably has a long capillary tip or needle.

The closure means may be provided with a constricted elution space between the tubular enclosure and the closure means membrane. The constricted elution space separates the gel pieces and the buffer in the tubular enclosure from the closure means membrane where electroeluted biomolecules are collected. The constricted elution space may be created by positioning a chamber or a porous septum between the tubular enclosure and the closure means membrane. The constricted elution space should have a capacity under 200 microliters, and preferably under 50 microliters.

The open ends of the tubular enclosure preferably have razor sharp edges to facilitate engaging pieces of the separating gel. If the tubular enclosure has demountable closure means, then both open ends of the tubular enclosure may be used for engaging pieces of gel and the two open ends may differ in the size of gel pieces the open ends engage. Preferably, the closure means is positioned over the end which engages the larger piece of gel.

The tubular enclosure and the closure means are preferably made of rigid and transparent materials which do not glow under ultra-violet (u.v.) light and preferably transmit u.v. light so that the DNA band may be observed by placing the tubular enclosure under u.v. light.

The method disclosed in the parent includes engaging the piece of separating gel containing the band of biomolecules intended for electroelution in the tubular enclosure by positioning the tubular enclosure over the separating gel directly above the band of biomolecules intended for electroelution. The tubular enclosure is then pushed through the soft separating gel thereby engaging the piece of separating gel containing the band of biomolecules intended for electroelution into the tubular enclosure. Preferably, the piece of separating gel is engaged into the tubular enclosure while the separating gel is submerged under the electrophoresis buffer. After engaging the separating gel piece, the piece is conveniently excised if the tubular enclosure is extracted from the separating gel by tilting it to a side.

After the piece of separating gel is engaged in the tubular enclosure the tubular enclosure is submerged in the electrophoresis tank. If the closure means is demountable from the tubular enclosure, after engaging the piece of separating gel in the tubular enclosure the closure means is capped on one or the tubular enclosure ends. Preferably no air bubbles are trapped in the tubular enclosure or the closure means. To avoid air bubble getting trapped in the tubular enclosure or the closure means, the tubular enclosure and the closure means should be filled with the electrophoresis buffer before being submerged in the electrophoresis tank. Preferably, the piece of separating gel is positioned close to the closure means or closure means membrane, allowing only a thin film of electrophoresis buffer between the gel piece and the closure means or closure means membrane. Preferably, the piece of separating gel in the tubular enclosure is pushed against the closure means or closure means membrane using a plunger type device (or plunger means), such as pipette tips or a bar. This forms the thin film of buffer between the gel piece and the closure means or closure means membrane.

As disclosed in the parent, after engaging the piece of separating gel in the tubular enclosure, the tubular enclosure is submerged in an electrophoresis tank such that the semipermeable closure means membrane faces the positive terminal. In fact, the tubular enclosure may be submerged in the same horizontal submerged electrophoresis device where the first or proceeding electrophoresis separation was performed. The tubular enclosure may be placed on top of the submerged separating gel.

When electrical current is applied to the electrophoresis tank the piece of separating gel engaged in the tubular enclosure experiences the electrophoresis electrical field. Biomolecules, such as protein and nucleic acids, in the piece of separating gel migrate toward the positive terminal and finally emerge out of the piece of gel into the buffer contained between the gel piece and the closure means membrane. Continuing the electrical field forces the biomolecules further toward the positive terminal which is blocked by the semipermeable dialysis membrane of the closure means. The semipermeable membrane prevents the migration of protein, nucleic acids and the like out of the tubular enclosure without hindering the electrophoresis electrical field, thereby concentrating protein and nucleic acids near the membrane. Because the nucleic acid molecules are visible under UV light, the migration can be followed under a UV lamp. The protein and nucleic acids accumulated near the closure means membrane may now be recovered with a pipette tip.

In the present invention, after electroelution is complete, the biomolecules accumulated against the closure means membrane may be recovered by rupturing the passage means with a sharp object, introducing a capillary pipette tip through the passage means to reach behind the closure means membrane. The pipette tip is preferably positioned along side the closure means membrane and the thin film of buffer (between the gel piece and the closure means membrane) containing the eluted biomolecules is removed. Any residual biomolecules may also be removed by applying a few drops of buffer or water on the gel piece and withdrawing the liquid with a pipette tip as described above.

The tubular enclosure and closure means of this invention accommodate electroelution in the same electrophoresis tank as where the first or preceding electrophoresis separation was performed. This eliminates the need for a separate electroelution device. The passage means of the present invention further assists the ease and accuracy of recovering the biomolecules.

BRIEF DESCRIPTION OF THE DRAWINGS

In the accompanying drawings which form a part of the specification and are to be read in conjunction therewith, and in which like reference numerals are used to indicate like parts in the various views:

FIG. 7 is an isometric view of a tubular enclosure having a piece of gel engaged in it and a closure means mounted at the end closer to the piece of gel;

FIG. 8 is an isometric view of an alternative embodiment of the tubular enclosure wherein the closure means is not demountable;

FIG. 9 shows the tubular enclosure of FIG. 6 submerged in an electrophoresis tank and placed on the top of the separating gel such that the closure means faces the positive terminal, and shows the hollowed part of the separating gel after removing a piece of separating gel with the tubular enclosure;

DETAILED DESCRIPTION OF THE PREFERRED EMBODIMENT

Figure 1:
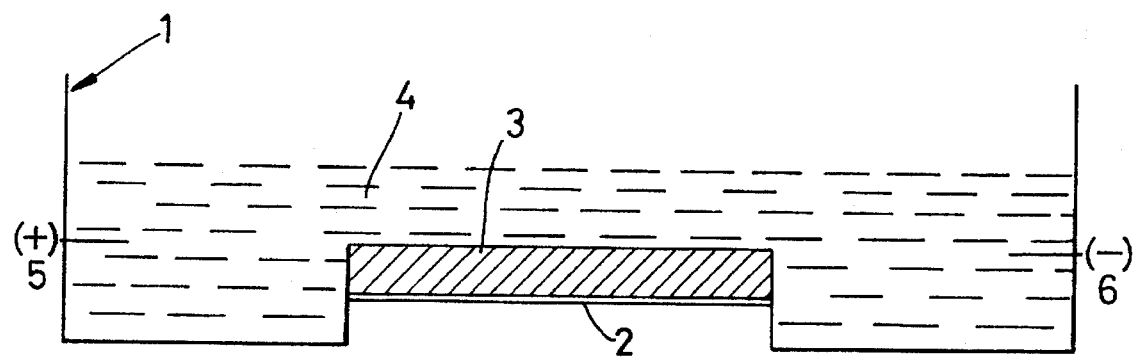
FIG. 1 is a front elevation view of a widely used submerged horizontal gel electrophoresis device.

As disclosed in the parent, the submerged horizontal electrophoresis device shown in FIG. 1 is one of the most widely used devices for separation of nucleic acids. The electrophoresis device has a reservoir tank 1 and a horizontal platform 2 for positioning a bed of separating gel 3 (or another biomolecule support medium) submerged under an electrophoresis buffer 4. Electric current is applied by positive and negative terminals 5 and 6, respectively. The separating gel 3 has preformed rectangular shaped wells (not shown) for loading samples containing biomolecules. When electric current is applied to the terminals, proteins and nucleic acids migrate toward the positive terminal and separate into distinct bands depending on their molecular size, the bands are substantially the same shape and size as the sample wells, i.e., rectangular. In the case of nucleic acids, the bands are visible under a UV lamp.

Figures 2, 3, 4:
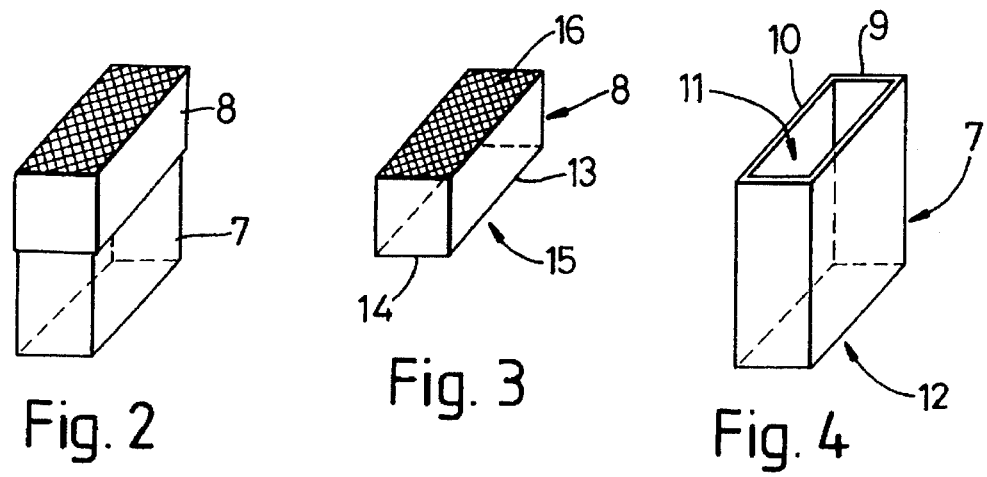
FIG. 2 is an isometric view of an embodiment of a tubular enclosure having a closure means.
FIG. 3 is an isometric view of the closure means for the tubular enclosure shown in FIG. 2.
FIG. 4 is an isometric view of a tubular enclosure without a closure means.

FIG. 2 shows an embodiment of the invention disclosed in the parent having a tubular enclosure 7 and a closure means 8. As shown in FIG. 4, the tubular enclosed 7 includes two parallel long sides 10 separated by two parallel short sides 9 forming a substantially rectangular interior shape for engaging a rectangular shaped piece of separating gel having a rectangular shaped band of biomolecules. The height of the tubular enclosure 7 is slightly taller than the thickness of the gel 3 it will be used to engage. (See FIG. 5.) The extended height of the tubular enclosure 7 makes it possible to manipulate the tubular enclosure while engaging the gel piece. In the preferred embodiment, the tubular enclosure 7 is open at both ends 11 and 12.

As shown in FIG. 3, the closure means 8 generally includes a tubular shape having two long parallel sides 13 separated by two short parallel sides 14, an open end 15, and another end sealed with a semipermeable dialysis membrane 16. The open end 15 of the closure means 8 is appropriately sized and shaped to fit snugly around opening 11 or 12 of the tubular enclosure 7. (See FIGS. 6 and 7).

Figures 5, 6:
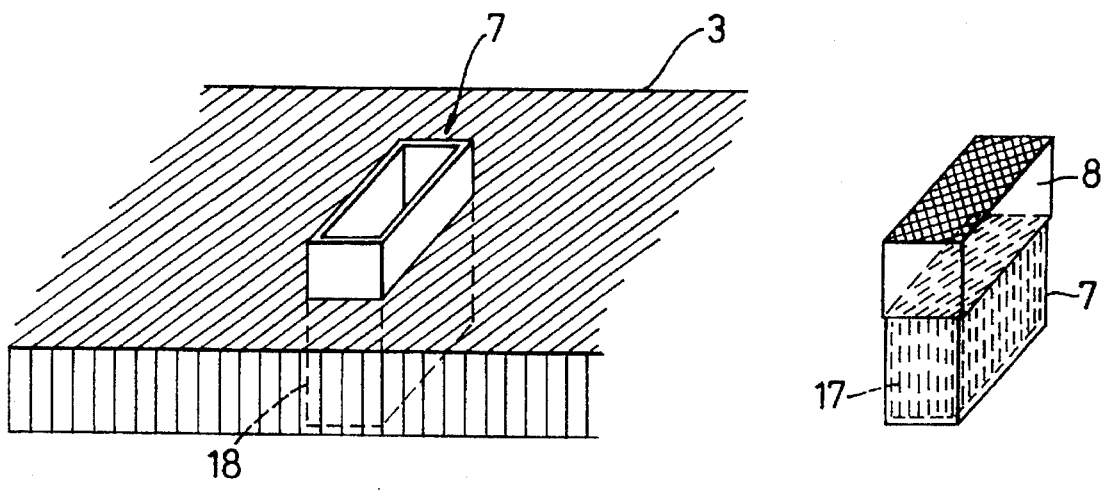
FIG. 5 shows the use of the tubular enclosure engaged into a piece of separating gel.
FIG. 6 is an isometric view of a tubular enclosure having a piece of separating gel engaged in it and a closure means mounted at the end opposite the piece of separating gel.

FIG. 5 shows the use of the tubular enclosure 7 for picking and engaging a piece of the separating gel 3. Preferably, the gel 3 is engaged while submerged under the electrophoresis buffer 4. The tubular enclosure 7 is placed over the separating gel 3 and positioned directly above a band of protein or nucleic acids (not shown) intended for electroelution. The enclosure 7 is pushed through the soft gel picking a rectangular piece of separating gel 17 in the process. The dotted line 18 in FIG. 5 shows the outline of the tubular enclosure 7 embedded in the separating gel. FIG. 6 illustrates the tubular enclosure after removing it from the gel. The piece of gel 17 is engaged within the inside walls of the tubular enclosure, leaving behind a rectangular hole 19 in the separating gel 3. (See FIG. 9). The demountable closure means 8 of FIG. 3 is used to close the open end of the tubular enclosure 7. The closure means can be positioned on either open end of the tubular enclosure 7 as shown in FIG. 6 and FIG. 7. In FIG. 6 the gel piece 17 is located at the end opposite the closure means membrane 16. In FIG. 7 the gel piece 17 is positioned close to the closure means membrane 16. A thin film of buffer is preferably formed between the gel piece 17 and the closure means membrane 16 and the closure means is preferably positioned on the open end which engages the gel, as shown in FIG. 7. This facilitates the piece of gel 17 being positioned close to the closure means membrane 16 and the creation on a thin film of electrophoresis buffer between the piece of gel 17 and the closure means membrane 16. The piece of gel may be pushed against the closure means membrane using a plunger type device or a plunger means, such as pipette tips (not shown), in order to create the thin film of buffer between the piece of gel and the closure means membrane.

As disclosed in the parent, the closure means 8 is preferably demountable. However, it is equally possible to permanently mount the closure means on the tubular enclosure 7. (See FIG. 8) FIG. 9 shows the tubular enclosure 7 containing a rectangular piece of gel 17, having a biomolecule band (not shown), submerged in the electrophoresis tank and placed on top of the separating gel 3 such that the semipermeable closure means membrane 16 faces the positive terminal 5. When electric current is applied across the electrophoresis tank, proteins and nucleic acids migrate toward the positive terminal and accumulate against the closure means membrane 16. The semipermeable closure means membrane 16 prevents the migration of protein and nucleic acid out into the buffer tank without hindering the electrophoresis electric field.

The migration of proteins and nucleic acids out of the gel piece 17 takes only a few minutes, however, the rate of migration is dependent on the size of the molecules, porosity of the gel, and the strength of the electric field. The migration of nucleic acids may be accelerated by increasing the strength of the electric field by 2–10 fold. When elution is performed at an elevated current there is risk of overheating. The overheating could be controlled by having a cooling system attached to the electrophoresis device. Alternatively, overheating could also be controlled by replacing the electrophoresis buffer with pre-chilled electrophoresis buffer and/or adding ice cubes made of the buffer. With DNA & RNA, the progress of elution can be monitored using a UV lamp. After elution is complete the proteins and nucleic acids are collected from the closure means 8 using a pipette tip. Prior to removing the biomolecules, the excess buffer is preferably removed from the tubular enclosure 7. The tubular enclosure 7 is then removed from the closure means 8 and the eluted biomolecules may be recovered from the closure means 8.

Figure 10:
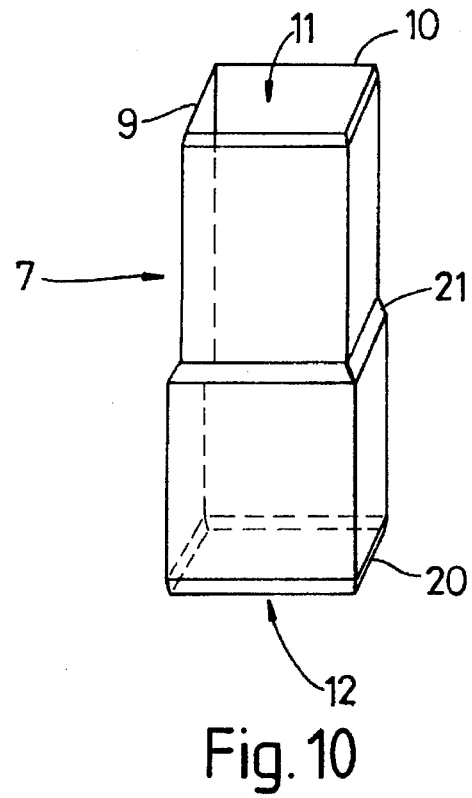
FIG. 10 shows an alternative embodiment of a tubular enclosure in which the two open ends have two different sizes for engaging gel pieces.

In the present invention, FIG. 10 shows an alternative embodiment of the tubular enclosure 7 in which the two open ends 11 and 12 have different sizes and therefore the open ends will engage gel pieces of two different sizes. This alternative tubular enclosure may be constructed by introducing an inflection 21 in the tubular enclosure (as shown in the drawing FIG. 10), or by introducing a slope construction between the two open ends (not shown). The open ends of the tubular enclosure preferably have razor sharp edges 20 to facilitate engaging pieces of the separating gel 3.

Figure 11A:
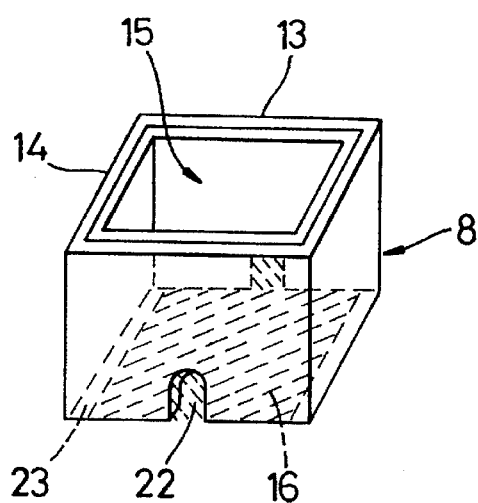
FIGS. 11a and 11b show the improved closure means of the present invention which include a passage means for reaching behind the closure means membrane.

In the present invention, the closure means 8 is provided with a passage means 22 (see FIGS. 11a and 11b), which provides an opening for reaching behind the closure means membrane 16. The passage means 22 may be sealed with the closure means membrane 16. After electroelution, the membrane may be ruptured with a sharp object and a pipette tip may be introduced through the passage means 22, behind and alongside the closure means membrane 16, to recover the biomolecules accumulated against the membrane 16. Any residual biomolecules may be removed by washing the gel piece 17 with a few drops of water or buffer and removing the liquid.

Figure 12A:
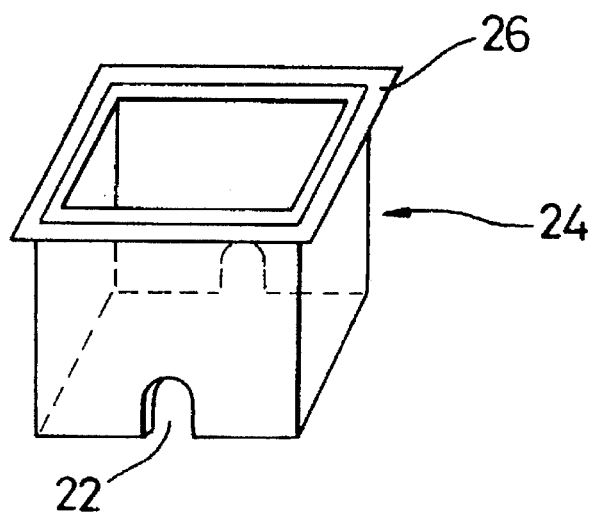
FIGS. 12a and 12b show the outer element and the inner element of the closure means shown in FIGS. 11a and 11b.
Figure 12B:
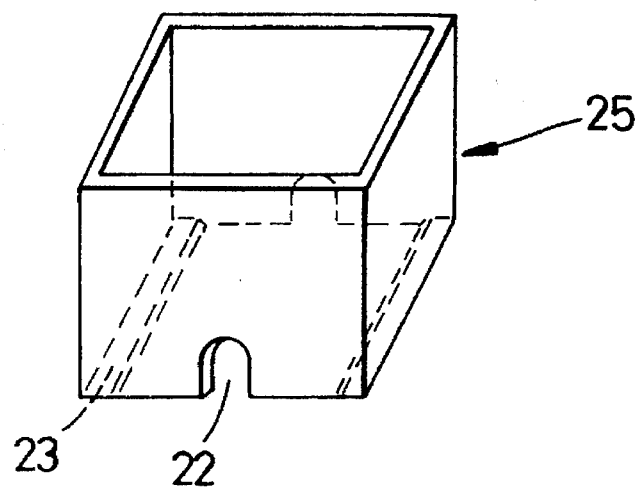

As shown in FIGS. 12a and 12b, the closure means 8 of the present invention includes an inner element 24, and an outer element 25. The inner element 24 includes a lip structure 26 and the passage means 22, while the outer element 25 (also refereed to as a sleeve member) includes the passage means 22 and a rest platform 23 which supports the inner element 24. The outer element 25 (sleeve member) is designed to sleeve over the inner element 24.

Figure 11B:
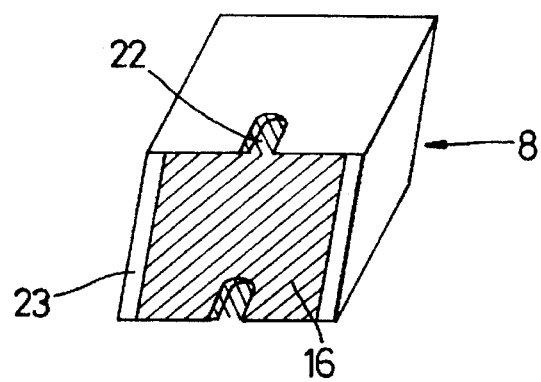

In operation, a piece of the dialysis membrane 16 is placed between the outer element 25 (sleeve member) and the inner element 24. The outer element 25 is sleeved over the inner element 24 such that the passage means 22 of the two elements align and secure the membrane 16 across the end opposite the open end 15. If desired, the closure means membrane 16 may be large enough to also cover the passage means 22, as shown in FIG. 11b. The closure means 8 may be positioned on either end of the tubular enclosure. Preferably, the closure means is positioned on the larger open end 12 of the tubular enclosure 7.

It is understood that the closure means having the passage means described herein (FIG. 11 and FIG. 12) may also be used with other types of tubular enclosure and reservoirs used for electroelution. The DNA recovered from the closure means retains all of its biochemical properties and is good for molecular biology work. Similarly, the protein recovered using the present invention maintains all of its biochemical properties. The method described in this invention can be used for proteins, nucleic acids, and other charged molecules.

Because the invention described herein does not require a separate electroelution device, the conventional horizontal electrophoresis device as shown in FIG. 1, may be provided with a platform having means for securely holding the tubular enclosure 7. Such a platform and securing means may be constructed on a side of the horizontal platform 2. The securing means could be a horizontal platform having a parallel second platform separated by spacers for holding the tubular enclosure.

The method described in this invention can be carried out either manually or automatically. In automatic operation, after electrophoresis, DNA bands are visible using either optical methods or chemical methods. The tubular enclosure 7, positioned in an arm, is automatically directed to engage and excise one of the DNA bands in the separating gel 3. The tubular enclosure having the piece of gel containing the DNA band for electroelution is then automatically fitted with the closure means 8 and subjected to electroelution.

It is also understood that the tubular enclosure without closure means, as shown in FIG. 10, may be used for excising pieces of gel independent of the electroelution method described in this invention.

While the present invention has been described by reference to a specific embodiment, it should be understood that modifications and variations of the invention may be constructed without departing from the spirit of the invention. The scope of the invention is defined solely by the claims, and their equivalents.

What is claimed is:

1. A method of electroelution of biomolecules following electrophoretic separation, the method comprising the steps of:

providing a piece of separating gel having bands of biomolecules formed by said electrophoretic separation;

engaging an enclosure into said separating gel such that at least one of said bands of biomolecules is secured within said enclosure;

capping said enclosure with a closure means;

submerging said enclosure with said closure means into an electrophoresis tank such that said closure means faces the positive terminal;

applying an electric field across said electrophoresis tank thereby forcing said biomolecules to migrate toward said positive terminal and accumulating said biomolecules at said closure means; and recovering said trapped biomolecules by inserting a capillary tip through a passage means adjacent an end of said closure means nearest said positive terminal.

2. The method according to claim 1 wherein said closure means includes an open end and an opposite end, said passage means being located adjacent said opposite end, and a membrane covers said opposite end and said passage means during application of said electric field, and wherein the step of recovering said biomolecules further including the steps of rupturing the membrane covering said passage means and inserting said capillary tip through said passage means such that said capillary tip is positioned behind said opposite side membrane.

3. The method according to claim 2 wherein said electrophoresis tank is filled with an electrophoresis buffer and the method further includes the step of filling said enclosure and said closure means with said electrophoresis buffer.

4. The method according to claim 3 wherein the step of submerging further includes the steps of submerging said enclosure with said closure means in the same device used for said electrophoretic separation and placing said enclosure with said closure means on top of said separating gel within said electrophoresis device.

5. The method according to claim 4 wherein the step of engaging said separating gel further includes the steps of positioning said enclosure over said separating gel directly above one of said bands of biomolecules and pushing said enclosure through said separating gel thereby engaging said gel into said enclosure.

6. A method for electroelution of biomolecules from a separating gel, the method comprising the steps of:

engaging a piece of a separating gel containing biomolecules with a shaped body having at least one open end, said engaging step comprising positioning the body over said separating gel, with said open end right above said biomolecules and pushing said open end into the separating gel thereby excising said gel piece from said gel and securing said gel piece into said body, wherein said body is operatively connected to a closure means; and separating said biomolecules from said gel piece by applying an electrical field to said gel piece to move said biomolecules toward said closure means.

7. A method according to claim 6, wherein said closure means comprises a membrane that is impermeable to said biomolecules and does not interfere with the electrical field.

8. A method according to claim 7, wherein said body has only one open end and said closure means is integral to said body and is located opposite said open end.

9. A method according to claim 6, wherein said closure means is detachably connected to said body, said closure means including an open end, an opposite end, and a membrane secured therein and further comprising capping said open end of said body with said closure means before said separating step.

10. A method according to claim 7, wherein said body comprises opposing first and second open ends, wherein said closure means is detachably connected to said body, said closure means including an open end, an opposite end, and a membrane secured therein, and further comprising capping one of said first and second open ends of said body with said closure means.

11. A method according to claim 6, wherein said body is thicker than said gel to facilitate manipulation of said body during said engaging step.

12. A method according to claim 10, wherein said capping step comprises placing the open end of said closure means on the open end of the body closest to said gel piece.

13. A method according to claim 7, further comprising pushing said gel piece against said membrane after said engaging step.

14. A method according to claim 6, wherein said separating step is carried out in the same electrophoresis device used for the preceding electrophoretic separation of biomolecules.

15. A method according to claim 6, wherein said body is tubular.

16. A method according to claim 15, wherein said biomolecules are separated into a plurality of bands having a defined shape and size within said separating gel and wherein said tubular body has an interior cross-section resembling said defined shape and size.

17. A method according to claim 15, wherein said open end has an interior cross-section which is rectangular in shape.

18. A method according to claim 6, wherein said body is made of a material which does not glow under ultraviolet light.

19. A method according to claim 6, wherein said open end of said body has at least one sharp edge to facilitate said engaging step.

20. A device for assisting electroelution of biomolecules from a separating gel, comprising:

a shaped body for retaining a piece of a gel containing biomolecules, said body having cutting means for engaging and excising said gel piece, said cutting means comprising at least one open end of said body; and a closure means for collecting said biomolecules after elution from said gel piece, said closure means comprising a membrane that is impermeable to said biomolecules and does not interfere with an electrical field, wherein said closure means is operatively connected to said shaped body.

21. The device of claim 20, wherein said body is tubular.

22. The device of claim 20, wherein said at least one open end of said body has at least one sharp edge to facilitate the engaging and excision of said gel piece.

23. The device of claim 20, wherein said closure means is integral to said body and is located opposite said open end.

24. The device of claim 20, wherein said closure means is detachably connected to said body and includes an open end, an opposite end, and a membrane secured therein.

25. The device of claim 24, wherein said opposite end is open and said membrane is secured over said opposite end.

26. The device of claim 24, wherein said body comprises opposing first and second open ends, at least one of said ends of said body being open and shaped and sized to be positioned within said open end of said closure means.

27. The device of claim 26, wherein each of said first and second ends is open.

28. The device of claim 27, wherein said first and second ends have interior cross-sections of the same size.

29. The device of claim 27, wherein said first and second ends have interior cross-sections of different sizes.

30. The device of claim 29, wherein the interior cross-section of said first end of said body is larger than the interior cross-section of said second end and only said first open end is capable of forming a snug fit with said closure means.

31. The device of claim 29, wherein the interior cross-section of said first end of said body is smaller than the interior cross-section of said second end of said body and only said second end is capable of forming a snug fit with said closure means.

32. The device of claim 20, wherein said open end has an interior cross-section that is rectangular in shape.

33. The device of claim 20, wherein said body is made of a material that does not glow under ultraviolet light.

34. The device of claim 20, wherein said closure means further comprises a passage means for accessing said biomolecules collected in said closure means.

35. The device of claim 34, wherein said passage means comprises at least one aperture adjacent to said membrane, said aperture being covered by a membrane that is impermeable to said biomolecules.

36. The device of claim 35, wherein said aperture is sized to accept a capillary tip to allow removal of said collected biomolecules.

37. The device of claim 24, wherein said membrane is secured over said opposite end by an outer element sleeved over an inner element.

38. The device of claim 37, wherein said closure means further comprises a passage means, said passage means comprising at least one aperture in each of said outer element and said inner element, said apertures being located and aligned with each other adjacent said opposite end, and wherein said apertures are covered by said membrane.

39. The device of claim 20, wherein said membrane is a dialysis membrane.

40. The device of claim 20, wherein said membrane is capable of binding said biomolecules.

41. The device of claim 20, wherein said membrane is an ion-exchange membrane.

42. A device according to claim 20, wherein said body is thicker than said gel to facilitate manipulation of said body during said engaging and removing steps.

43. A device for collecting and recovering biomolecules following electroelution of biomolecules from a gel, comprising:

a shaped closure having opposing first and second open ends, said first open end being shaped and sized to be operatively connected to a tubular shaped reservoir adapted for electroeluting biomolecules from a piece of a gel;

a membrane secured over said second open end;

a passage located in said closure adjacent to said second open end and is covered by a portion of said membrane, said membrane being rupturable to provide access to electroeluted biomolecules collected at said second end;

wherein said membrane is secured over said second open end and said passage by an outer element sleeved over an inner element, and wherein said membrane is impermeable to said biomolecules and does not interfere with an electrical field.

* * * * *